(12) United States Patent
Lombardo et al.

(10) Patent No.: US 6,548,307 B2
(45) Date of Patent: Apr. 15, 2003

(54) DETERMINATION OF LOGP COEFFICIENTS VIA A RP-HPLC COLUMN

(75) Inventors: Franco Lombardo, Gales Ferry, CT (US); Marina Y. Shalaeva, Old Lyme, CT (US); Karl A. Tupper, Chicago, IL (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/782,428

(22) Filed: Feb. 13, 2001

(65) Prior Publication Data

US 2002/0009388 A1 Jan. 24, 2002

Related U.S. Application Data

(60) Provisional application No. 60/182,353, filed on Feb. 14, 2000.

(51) Int. Cl.$^7$ ................................. G01N 30/34

(52) U.S. Cl. ..................... 436/161; 73/61.52; 73/61.56; 210/656; 210/662

(58) Field of Search ......................... 436/161; 73/61.52, 73/61.56; 210/656, 662

(56) References Cited

PUBLICATIONS

Minick et al, J. Med. Chem., vol. 31 (1988) pp. 1923–1933.*
Britto et al, Chromatographia, vo. 53, No. 1/2 (2001), pp. 11–16.*
Pagliara et al, J. Liq. Chromatography, vol. 18 (1995), pp. 1721–1745.*

* cited by examiner

*Primary Examiner*—Jan Ludlow
(74) *Attorney, Agent, or Firm*—Peter C. Richardson; Paul H. Ginsburg; Israel Nissenbaum

(57) ABSTRACT

This invention provides a RP-HPLC method, for the determination of $logP_{oct}$ values, which combines ease of operation and high accuracy, and which has been shown to work for a set of 36 molecules largely comprised of drugs. The general features of the method are: i) compound sparing ($\leq 1$ mL of a 30-50 $\mu$g/mL solution needed), ii) rapid determinations (20 minutes on average), iii) low sensitivity to impurities, iv) wide lipophilicity range (6 $logP_{oct}$ units), v) good accuracy, vi) excellent reproducibility. A linear free energy relationship (LFER) analysis, based on solvation parameters, shows that the method encodes the same information obtained from a shake-flask $logP_{oct}$ determination. The value generated via this method is referred to as $ElogP_{oct}$.

8 Claims, 3 Drawing Sheets

DETERMINATION OF LOGP COEFFICIENTS VIA A RP-HPLC COLUMN

CROSS-REFERENCE TO RELATED APPLICATION

This application claims priority of U.S. provisional application No. 60/182,353, filed Feb. 14, 2000.

BACKGROUND OF THE INVENTION

1. Field of the Invention

This invention is related to an improved method for determination of $logP_{oct}$ values for drug candidates.

2. Related Art

The importance of octanol-water partition coeffiecients ($logP_{oct}$) is underscored, for example, by the generally observed correlation between a high lipophilicity ($logP_{oct}$>4.5) and a poor solubility.[1] Computed values for drug molecules are often inaccurate, depending on the software used, by as much as two $logP_{oct}$ units, for any given compound or class of compounds. Data analyses and alerts such as the Lipinski's "Rule-of-5"[2] would greatly benefit by the introduction of measured values, especially if they could be generated with high speed and accuracy. Thus, whenever possible, the computed values should be replaced by measured values, especially if the method requires only a very small amount of a new chemical entity, and can tolerate some impurities.

Lipophilicity of drug candidates is important since it is being used in the prediction of absorption, disposition and excretion.[3] It is generally held that very lipophilic compounds are "preferred" targets for metabolism, often leading to high clearance values and frequently correlates with a high plasma protein binding. A large volume of distribution, probably due to a high fraction of the compound bound to tissues, is often observed in the case of lipophilic compounds. Thus, a method that can accurately and rapidly yield $logP_{oct}$ values, is an important addition to the experimental tools available for physicochemical properties screening.

The classical shake-flask method, or variations of this method which have been described,[4] are neither rugged not rapid enough for medium to high-throughput applications, and they are generally sensitive to impurities, and less amenable to automation than are reverse phase high performance liquid chromatography (RP-HPLC) methods.[5]

(RP-HPLC) retention data have been shown to correlate well with absolute and relative lipophilicity values but, they have also been criticized as not being a true "replacement" for shake-flask values.[4] Part of the criticism stems from the fact that many reports were limited in their scope, focusing either on fairly simple monofunctional solutes,[6-7] or classes of analogs[8] with a limited $logP_{oct}$ range. Furthermore, in several cases[4], the slope of the $logP_{oct}$ vs. log k' or log k'$_w$, solvent was quite different from unity, casting doubts about the different balance of forces responsible for the two values. In these linear regression analyses, k' represents the capacity factor of the solute at a given concentration of organic solvent, and k'$_w$ is the capacity factor extrapolated to 0% of the organic solvent. However we have found that, with a judicious choice of conditions, RP-HPLC methods might be defined, following Taylor[9], as "being in a class of their own".

Another factor of great importance,[5] is the reproducibility of the data from column to column, that is the reproducibility is likely to be dependent on packing chemistry and manufacturing of the columns. It might be argued that a pooling data from different columns will not be difficult, although "scaling standards" might be needed. However, tests of reproducibility of the method from column to column should be performed, independently of the above arguments.

The speed of the determination and the ability to handle diverse structures and lipophilicity values are, of course, of paramount importance in an industrial research setting. These aspects translate into the capability of screening, with fairly modest resources, a fairly large number of compounds, with a good degree of accuracy applicable across a wide range of lipophilicity values.

There is a long felt need for a method for determining $logP_{oct}$ which would be accurate, rapid and possess a good dynamic range, together with being applicable to a variety of drug-like molecules.

REFERENCES

1. Yalkowski, S. H.; Valvani, S. C. Solubility and Partitioning I: Solubility of Nonelectrolytes in Water. J. Pharm. Sci. 1980, 69, 912-922.
2. Lipinski, C. A.; Lombardo, F.; Dominy, B. W.; Feeney, P. J. Experimental and computational approaches to estimate solubility and permeability in drug discovery and development. Adv. Drug. Del. Rev. 1997, 23, 3-25.
3. Smith, D. A.; Jones, B. C.; Walker, D. K. Design of Drugs Involving the Concepts and Theories of Drug Metabolism and Pharmacokinetics. Med. Res. Rev. 1996, 16, 243-266.
4. Sangster, J. Octanol-Water Partition Coefficients: Fundamentals and Physical Chemistry. Wiley, New York, 1997; pp. 79-112.
5. van de Waterbeemd, H. M.; Kansy, M.; Wagner, B.; Fischer, H. Lipophilicity Measurements by Reversed-Phase High Performance Liquid Chromatography (RP-HPLC). In Lipophilicity in Drug Action and Toxicology, Ch. 5, Pliska, V., Testa, B., van de Waterbeemd, H., Eds.; VCH: Weinheim, 1996; pp 73-87
6. Pagliara, A.; Khamis, E.; Trinh, A.; Carrupt, P.-A.; Tsai, R.-S.; Testa, B. Structural Properties Governing Retention Mechanisms on RP-HPLC Stationary Phases used for Lipophilicity Measurements. J. Liq. Chromatogr. 1995, 18,1721-1745.
7. Minick, D. J.; Frenz, J. H.; Patrick, M. A.; Brent, D. A. A Comprehensive Method for Determining Hydrophobicity Constants by Reversed-Phase High-Performance Liquid Chromatography. J. Med. Chem. 1988, 31, 1923-1933
8. Morelock, M. M.; Choi, L. L.; Bell, G. L; Wright, J. L. Estimation and Correlation of Drug Water Solubility with Pharmacological Parameters Required for Biological Activity. J. Pharm. Sci. 1994, 83, 948-952.
9. Taylor, P. J. Hydrophobic Properties of Drugs. In Comprehensive Medicinal Chemistry, Hansch, C., Sammes, P. G., Taylor, J. B. Eds.; Pergamon Press: Oxford, 1990; pp 241-294.
10. The LC-ABZ column is considered to be "RP-18 like" and it is electrostatically coated to decrease the solute interactions with free silanols. Pagliara, A.; Khamis, E.; Trinh, A.; Carrupt, P.-A.; Tsai, R.-S.; Testa, B. Structural Properties Governing Retention Mechanisms on RP-HPLC Stationary Phases used for Lipophilicity Measurements. J. Liq. Chromatogr. 1995, 18,1721-1745.
11. Minick, D. J.; Brent, D. A.; Frenz, J. Modeling Octanol-Water Partition Coefficients by Reversed-Phase Liquid Chromatography. J. Chromatogr. 1989, 461, 177-191.
12. Melander, W.; Stoveken, J.; Horvath, C. Stationary Phase Effects in Reversed-Phase Chromatography. I. Comparison of Energetics of Retention on Alkyl-Silica Bonded Phases. J. Chromatogr. 1980, 199, 35-56.

13. Valko K.; Bevan, C.; Reynolds, D. Chromatographic Hydrophobicity Index by Fast-Gradient RP-HPLC: A High-Throughput Alternative to log P/logD. Anal. Chem. 1997, 69, 2022-2029.
14. Abraham, M. H.; Chadha, H. S.; Leitao, R. A. E.; Mitchell, R. C.; Lambert, W. J.; Kaliszan, R.; Nasal, A.; Haber, P. Determination of solute lipophilicity as logP (octanol) and logP (alkane) using poly(styrene-divinylbenzene) and immobilised artificial membrane stationary phases in reversed-phase high performance liquid chromatography. J. Cromatogr. A. 1997, 766, 35-47.
15. Abraham, M. H.; Chadha, H. S.; Whiting, G. S.; Mitchell, R. C. Hydrogen Bonding. 32. An Analysis of water-Octanol and Water-Alkane partitioning and the ElogP Parameter of Seiler. J. Pharm. Sci. 1994, 83, 1085-1100.
16. Slater, B.; McCormack, A.; Avdeef, A.; Comer, J. E. A. pH-Metric log P. 4. Comparison of Partition Coefficients Determined by HPLC and Potentiometric Methods to Literature Values. J. Pharm. Sci. 1994, 83, 1280-1283.
17. Jezequel, S. G. Fluconazole: Interspecies Scaling and Allometric Relationships of Pharmacokinetic Properties. J.Pharm.Pharmacol. 1994, 46, 196-199.
18. Fujita, T.; Iwasa, J.; Hansh, C. A new substituent constant, $\pi$, derived from partition coefficients. J. Am. Chem. Soc.1965, 86, 5175-5180.
19. Rotonda, M. I.; Amato, G.; Barbato, F.; Silipo, C.; Vittoria, A. Relationship between octanol-water partition data, chromatographic indices and their dependence on pH in a set of nonsteroidal anti-inflammatory drugs. Quant. Struct. Act. Relat. 1983, 2, 168-173.
20. Bundgaard, H.; Falch, E. Allopurinol prodrugs. II. Synthesis, hydrolysis kinetics and physicochemical properties of various N-acyloxylmethyl allopurinol derivatives. Intern. J. Pharmaceut. 1985, 24, 307-325.
21. Lacko, L.; Wittke, B. The affinities of benzodiazepines to the transport protein of glucose in human erythrocytes. Arzneim. Forsch. 1984, 34, 403-407.s
22. Henczi, M.; Nagy, J.; Weaver, D. F. Determination of octanol-water partition coefficients by an HPLC method for anticonvulsant structure-activity studies. J. Pharm. Pharmacol. 1995, 47, 345-347.
23. Hansch, C.; Leo, A.; Hoekman, D. Exploring QSAR. Hydrophobic, Electronic, and Steric Constants. American Chemical Society: Washington, DC; 1995; pp. 3-216.
24. Tomida, H.; Yotsuynagi, T.; Ikeda, K. Solubilization of steroid hormones by polyoxyethylene lauryl ether. Chem. Pharm. Bull. 1978, 26, 2832-2837.
25. Seiler, P.; Zimmermann, I. 5-phenyl-1,3-dihydro-1,4-benzodiazepin-2-ones. Arzneim. Forsch. 1983, 33, 1519-1522.
26. Graf, E.; EI-Menshawy, M. pK- and Vk-messungen and Benzodiazepinen. Pharm. Uns. Zeit. 1977, 6, 171-178.
27. Schutz, V. H.; Fitz, H. Screening, detection and biotransformation of Lormetazepam, a new hypnotic agent from the 1,4-benzodiazepine series. Arzneim.-Forsch. 1982, 32, 177-183.
28. Iwasa, J.; Fujita, T.; Hansch, C. Substituent constants for alophatic functions obtained from partition coefficients. J. Med. Chem. 1965, 8, 150-153.
29. Okada, J.; Esaki, T.; Fujieda K. C-13 nuclear magnetic resonance spectra of antipyrine derivatives and their application to Hansch analysis. Chem. Pharm. Bull. 1976, 24, 61-71.
30. Anderson, R. F.; Patel, K. B. Effect of lipophilicity of nitroamidazoles on radiosensitization of hypoxic bacterial cells in vitro. Br. J. Cancer 1979, 39, 705-710.
31. Adams, G. E.; Clarke, E. D.; Flockhart, I .R.; et al. Structure-activity relationships in the development of hypoxic cell radiosensitizers. I. Sensitization efficiency. Int. J. Radiat. Biol. 1979, 35, 2, 133-150.
32. Mohler, V. W.; Soder, A. On chemistry and synthesis of 3,7-dimethyl-1-(5-oxo-hexyl)-xanthine. Arzneim. Forsch. 1971, 21, 1159-1160.
33. Hansch, C.; Nakamoto, K.; Gorin, M.; et al. Structure-activity relationship of chloramphenicols. J. Med. Chem. 1973, 16, 917-922.
34. Leo, Albert J. Chem. Rev. 1993, 1281-1306.
35. Waters Corporation, 34 Maple Street, Milford, Mass. 01757.

SUMMARY OF THE INVENTION

This invention provides a method of determining an experimental $logP_{oct}$, herein designated $ElogP_{oct}$ for a chemical compound which comprises: introducing said chemical compound to the column of a reverse phase high performance liquid chromatograph; said column being an embedded amide functional group column; or a C-18 bonded column with low silanol activity[35]; and eluting said compound with a mobile phase containing MOPS buffer and a methanol/octanol mixture in which the proportions of said methanol/octanol mixture to said buffer are from 70 to 15% v/v; and with the proviso that said mobile phase does not contain an aliphatic amine; and detecting the retention time required to elute said sample from said column; and calculating $ElogP_{oct}$ from the retention time of said sample; and decrease the overall time.

In a preferred method, in order to optimize the time of single measurements, the compounds for which $ElogP_{oct}$ is to be determined are divided into groups according to calculated lipophilicity based on chemical structure[34].

In a further preferred method, samples are divided into three log $P_{oct}$ ranges from –0.5 to 1; 1 to 3; and greater than 3.

Column conditions and % methanol in MOPS buffer were determined as follows:

| $logP_{oct}$ Range | Flow rate (mL/min) | % MeOH |
| --- | --- | --- |
| –0.5 to 1 | 0.5 | 15, 20, 25 |
| 1–3 | 1 | 40, 45, 50 |
| >3 | 2 | 60, 65, 70 |

Preferably, the entire group of samples in a given range of calculated $logP_{oct}$ is run before the column is equilibrated to the next condition.

A further preferred method is calculating $logP_{oct}$ values based on chemical structures by a programmed computer and introducing samples in a defined $logP_{oct}$ range into said column by robotic means under the control of a programmed computer and calculating $ElogP_{oct}$ from the retention time of the sample by equation 3.

DETAILED DESCRIPTION OF THE INVENTION

Minick at al,[7,11] used a MC-8 column, coupled with the addition of 1-octanol to both components of the eluent, together with the addition of small amounts of n-decylamine in the aqueous phase. Supelcosil columns such as Supelcosil ABZ/ABZ+ and Discovery RP-amide 16 also known as embedded amide functional group columns do not require a modifier such as n-decylamine. Octanol was useful to reproduce the intermolecular interactions experienced by a solute in a classical "shake-vial" octanol/buffer partition determination, while reducing the retention times. This invention "combines" the column used by Pagliara et al.,[6] with the conditions used by Minick et al,[7] with the exception of the use of n-decylamine, and extends its application to a set of diverse drug-like compounds. We also used an appropriate flow rate for each type of lipophilicity. The value generated by this method is referred to as $ElogPo_{oct}$.

Figure 1:
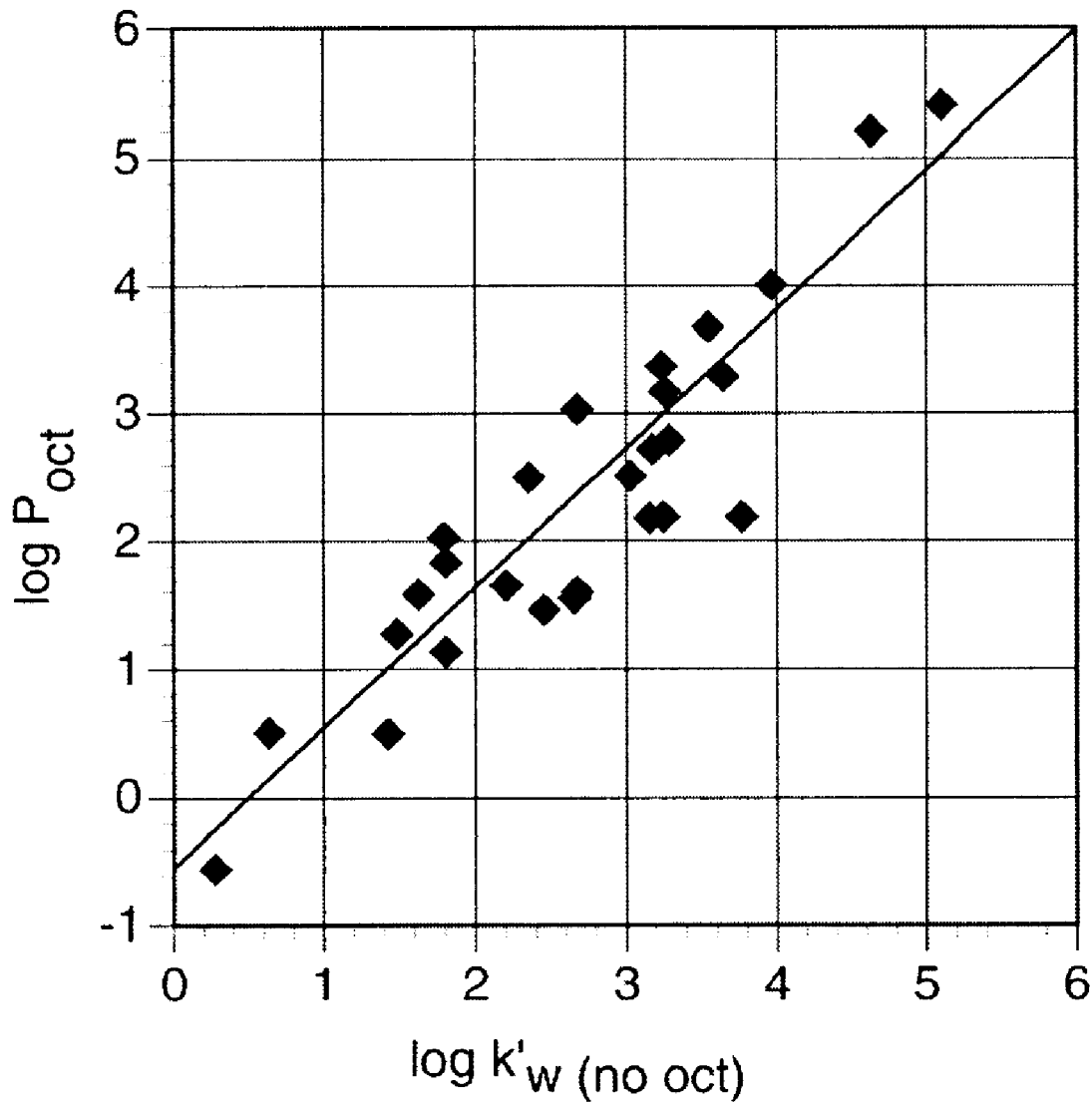
FIG. 1. Correlation between $logP_{oct}$ and log $k'_w$ in the absence of octanol.
Figure 2:
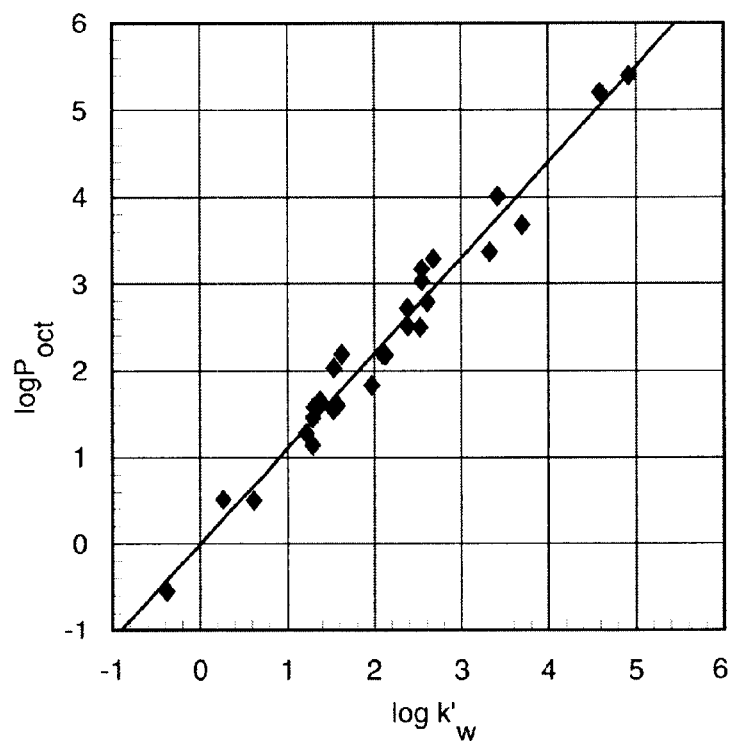
FIG. 2. Correlation between $logP_{oct}$ and log $k'_w$ in the presence of octanol.

The data obtained for an initial set of 27 compounds, in the absence or presence of octanol, pointed to a clear difference in performance, as shown by FIGS. 1 and 2, and by their respective equations. The compounds used are the first 27 compounds reported in Table 1. The data used in FIG. 1 were generated using only methanol and Morpholino Propane Sulfonic Acid (MOPS) buffer as the mobile phase, as opposed to FIG. 2, where octanol was added to methanol, and octanol-saturated water was used to prepare the buffer. Different columns were used for these runs, but the inter-column variability was checked (data not shown), and an excellent correlation was obtained for the three different columns. In one case, the same column was tested initially and after 4 months of intensive use, with significant difference. This established that the difference in performance was due to the addition of octanol to both components of the mobile phase, and not by potential differences in the column packing.

FIGS. 1 and 2 clearly bring out the significant difference between the addition of 1-octanol to the mobile phase (both components), with respect to the data generated in its absence. In both cases the slope is close to unity, but the error is more than doubled in the absence of 1-octanol as expressed by Eq. 1 and Eq. 2. In both cases a range of 6 $logP_{oct}$ units is encompassed by these experiments.

$logP_{oct}=1.0890(\pm0.0969)\log k'_w-0.5435(\pm0.2768)$ $N=27, R^2=0.835, R=0.914, s=0.556, F=126, q^2=0.808$ (Eq. 1)

$logP_{oct}=1.1014(\pm0.0389)logk'_w-0.0045(\pm0.0941)$ $N=27, R^2=0.970, R=0.985, s=0.238, F=803, q^2=0.965$ (Eq. 2)

The question of the value of the slope has been stressed by Minick et al.[11] Pointing to the work of Melander et al.,[12] these authors state that " . . . equations correlating log $k'_w$ and $logP_{oct}$ data represent linear free energy relationships in which the slope is an estimate of how closely the free energies of the processes compare." A slope close to unity implies that the two processes are homoenergetic, i.e. the free energy changes are the same. In the present case, a slope very close to unity was obtained with or without 1-octanol. Furthermore, a larger slope would result in the magnification of any error in the determination of log $k'_w$ if the estimation of $logP_{oct}$ was the final goal. The log $k'_w$ data could be used as a self-consistent scale of lipophilicity and, in this case, the second consideration would not be very important. An example might be represented by the work of Valko et al.,[13] which describes a chromatographic hydrophobicity index (CHI), obtained via a gradient run. In this case a correlation with a "classical" shake flask $logP_{oct}$ was not necessarily sought, and a self-consistent CHI scale was established. However, $logP_{oct}$ (or $logD_{oct}$) data are so widely used in many correlations by the medicinal chemistry community, that a "classical" $logP_{oct}$ value is likely to be desired.

The correlation was expanded by adding more drug compounds, aiming at expanding the physicochemical diversity of the set. Nine more compounds were added as reported in Table 1. At the same time an analysis of the data and the column performance, via the well-known salvation parameters of Abraham[14-15], was performed to answer the question of closeness between the classical shake flask $logP_{oct}$ values, and RP-HPLC derived values, beyond what could be surmised by a slope close to unity.

Figure 3:
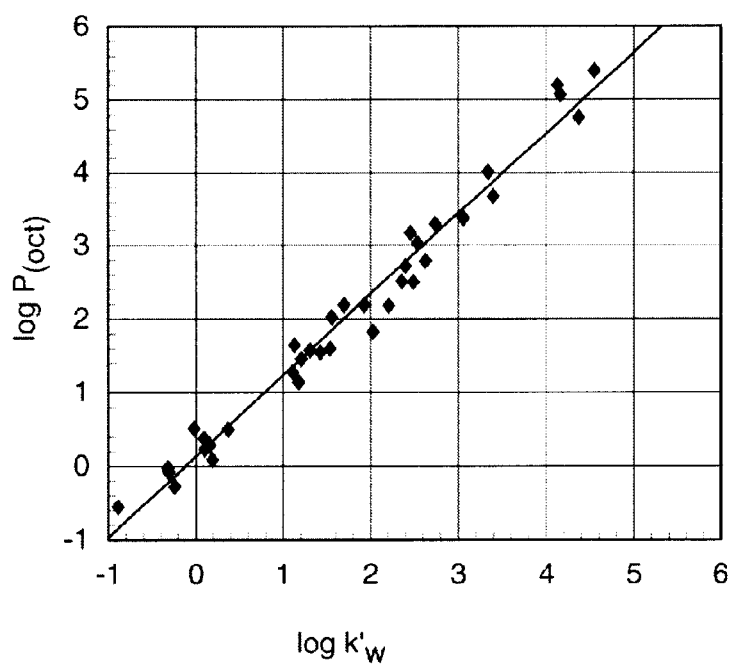
FIG. 3. Correlation between $logP_{oct}$ and log $k'_w$ for 37 solutes.

First, Eq. 3 shows that the correlation is excellent, and the predictive power of the method, expressed by the $q^2$ value, is also very good. FIG. 3 shows graphically the correlation between the shake-flask and the RP-HPLC data. Also the slope shown by Eq. 3 is very similar to the slope in Eq. 2, further demonstrating the accuracy of the method, and yielding an indirect assessment of its robustness in predicting unknown compounds. The cross-validated coefficient of determination, or $q^2$ value, shows the excellent predictive power of this method. The correlation was obtained by averaging the values obtained, for each compound, using three different columns.

$logP_{oct}=1.1021(\pm0.0291)logk'_w+0.1344(\pm0.0653)$ $N=36, R^2=0.977, R=0.988, s=0.251, F=1434, q^2=0.974$ (Eq. 3)

Figure 4:
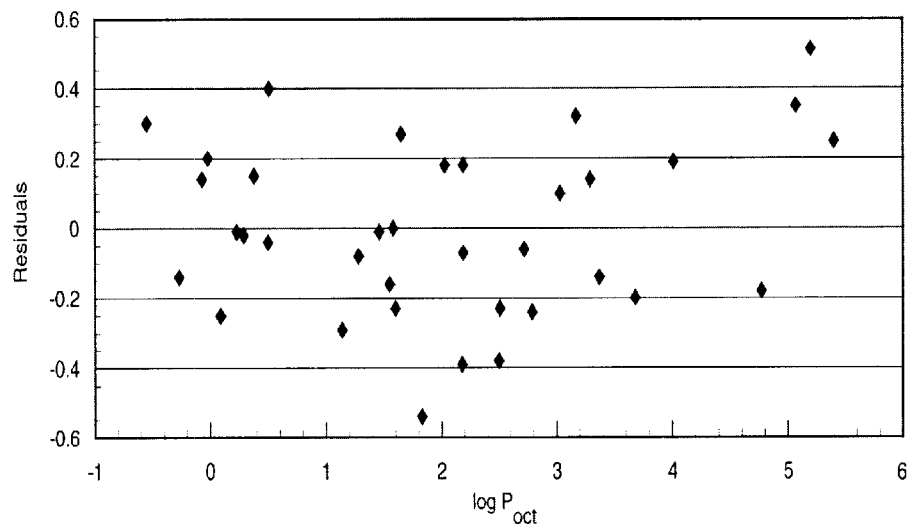
FIG. 4. Plot of residuals vs. $logP_{oct}$
Figure 5:
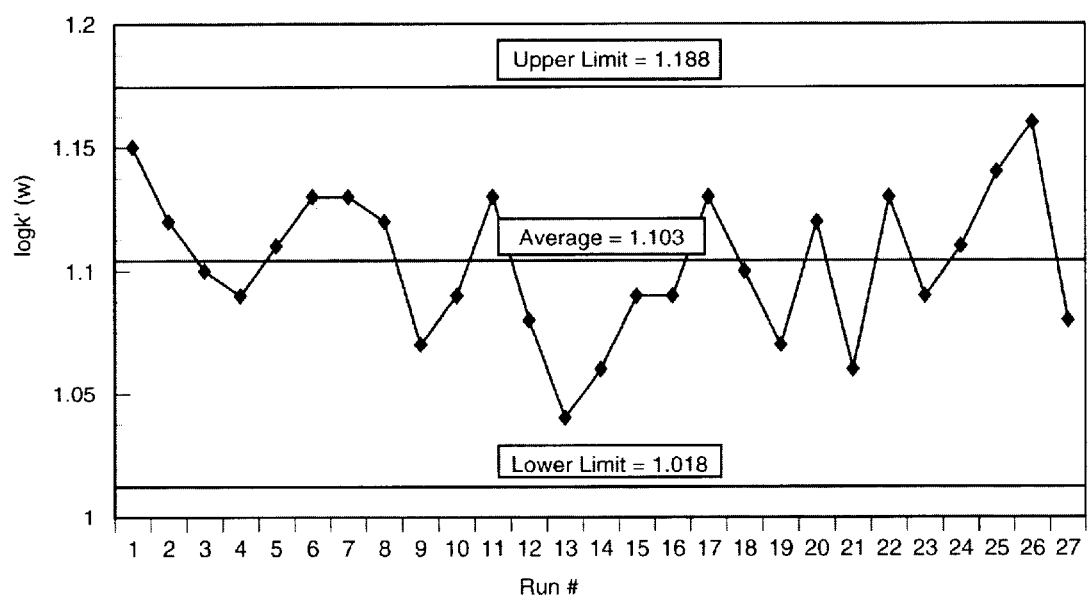
FIG. 5. Control plot for nifuroxime.

Furthermore it is worth noting that a plot of residuals vs. the $logP_{oct}$ values, as in FIG. 4, shows that the error distribution is very consistent across the entire range, and no curvature (larger error) is observed at extreme values. This is important because it shows that similarly accurate determinations can be obtained across 6 $logP_{oct}$ units. As a further measure for a day-to-day system suitability check, we used control charts, as shown in FIG. 5 for nifuroxime, constructed for ten compounds suitably chosen across the entire range. An unexpected variation in these plots would immediately "flag" questionable results. The values obtained via Eqn. 3 were designated as $ElogP_{oct}$, and referred to them as such in this document.

An analysis of the balance of forces underlying these phenomena, using a linear free energy relationship, based on salvation parameters was conducted, as described by Abraham.[14-15] In these equations R is the excess molar refraction, $\pi_2^H$ is the dipolarity/polarizability, $\Sigma\alpha_2^H$ and $\Sigma\beta_2^0$ are the (summation) hydrogen bond acidity and basicity, respectively, and $V_x$ is the McGowan's volume. In particular the superscript "0", used for the hydrogen-bonding basicity parameter, refers to a particular scale of values, useful for certain types of solutes, when the organic portion of the binary system is a partially miscible solvent, as in the case of water-saturated octanol. The other subscripts and superscripts have the usual meaning, i.e. they refer to hydrogen bonding scales and to the solute.[5] The calculated parameters are reported in Table 2, and the coefficients for the respective equations (Eq. 4 and 5), whether log $k'_w$ or $ElogP_{oct}$ values are used, are close (for log $k'_w$) or essentially identical (for $ElogP_{oct}$) to the coefficients of the equation based on shake-flask $logP_{oct}$ values (Eq. 6), as reported by Abraham, for 613 solutes.[15] However, the ratios of coefficients, normalized to the $V_x$ coefficient, are essentially identical for all three equations (data not shown). We conclude that the $ElogP_{oct}$ values, obtained using the method presented here, and expressed by Eq. 3, are identical to shake-flask values, but they can be generated at a much higher throughput, and combine ease of operation with a wide dynamic range. Due to lack of other partition data, and perhaps to a difficulty brought about by a possible push-pull effect in the case of nifuroxime, we were not able to obtained accurate parameters for this compound and 6-mercaptopurine, and these two solutes were excluded from the correlation.

$$log k'_w = 0.062 + 0.409 R_2 - 0.955\pi_2^H - 0.040\alpha_2^H - 3.092\Sigma\beta_2^0 + 3.485 V_x$$

$$N=34, R^2=0.980, R=0.989, s=0.225, F=276, q^2=0.967 \quad \text{(Eq. 4)}$$

$$ElogP_{oct} = 0.199 + 0.452 R_2 - 1.053\pi_2^H - 0.044\Sigma\alpha_2^H - 3.411\Sigma_2^0\beta + 3.843 V_x$$

$$N=34, R^2=0.980, R=0.989, s=0.248, F=276, q^2=0.967 \quad \text{(Eq. 5)}$$

$$log P_{oct} = 0.088 + 0.562 R_2 - 1.054\pi_2^H - 0.034\Sigma\alpha_2^H - 3.460\Sigma\beta_2^0 + 3.814 V_x$$

$$N=613, R^2=0.995, R=0.997, s=0.116, F=23162 \quad \text{(Eq. 6)}$$

As a further improvement, the calculation procedure was automated through in-house software to obtain the final $ElogP_{oct}$ value, without any manual intervention from the chromatographic data file. This modification allows for an enhanced throughput, starting with an already rapid procedure. $ElogP_{oct}$ data for any compound are obtained, on average, in 20 minutes or less, on a single instrument.

The current method is, at the moment, limited to neutral or weakly acidic or basic compounds, but it covers the practical limitation involved in the determination of compounds which are devoid of any significant ionization, within a reasonable range of pH, and thus are not amenable to a $logP_{oct}$ determination via well-known potentiometric techniques.[16]

By a judicious choice of mobile phase and RP-HPLC column, a very accurate $logP_{oct}$ determination method has been developed, which is characterized by rapid throughput, ruggedness and minimal manual intervention set forth in the introduction, for drug-like compounds. Since $logP_{oct}$ has been shown to be an important parameter for the ADME profiling of new chemical entities,[3] such as estimation of solubility, intestinal permeability and clearance, this method is useful for applications in pharmaceutical discovery and development settings.

Materials and methods. All the solutes were purchased directly from commercial sources (Aldrich, Sigma and Fluka) and used as received. Fluconazole was obtained internally. De-ionized water, HPLC grade methanol (J. P. Baker) and 1-octanol (Fisher scientific) were used throughout.

The mobile phase consisted, in all cases, of 20 mM MOPS buffer at pH 7.4, and methanol in varying proportions from 70 to 15% v/v. A 0.25% (v/v) amount of octanol was added to methanol, and octanol-saturated water was used to prepare the buffer, with the exception of the correlation obtained without octanol in either component of the mobile phase (vide infra). The capacity factors data ($k'=(t_R-t_0)/t_0$) obtained at various amounts of methanol were then extrapolated to 0% methanol and reported as $log k'_w$, using a linear procedure. In all cases, except for allopurinol ($R^2=0.96$) the coefficient of squared correlation was =0.99. Injections of pure methanol were used to determine $t_0$, i.e. the dead time, while $t_R$ has the usual meaning of the retention time for the analyte.

All the chromatographic runs were performed on a HP-1100 HPLC ChemStation at the ambient temperature. The columns used were Supelcosil LC-ABZ, 5μm, 4.6×50 mm. A diode array detector was used to monitor signals at 235, 255, 265 and 275 nm. Columns having different silica bond lots were tested to ensure reproducibility. Samples were dissolved in 1:1 methanol/water at a concentration of 10-30 μg/mL. The flow rate was 0.5, 1 or 2 mL/min, depending on the lipophilicity range. Three lipophilicity ranges were established using, in all cases, three points for the extrapolation to $k'_w$, as described in the table below.

| $logP_{oct}$ Range | Flow rate (mL/min) | % MeOH |
|---|---|---|
| −0.5 to 1 | 0.5 | 15, 20, 25 |
| 1–3 | 1 | 40, 45, 50 |
| >3 | 2 | 60, 65, 70 |

The samples were placed in the appropriate range by estimating their lipophilicity via computed values, or by prior experience with a given class. In each case the entire group of samples was run before the column is equilibrated to the next condition, in an automated fashion, and the initial estimation need not be very accurate. The data analysis was automated via in-house software yielding the $ElogP_{oct}$ values, directly from the chromatographic data files.

The shake-flask $logP_{oct}$ data were taken from the literature or determined in-house, except when data were not available or could not be determined experimentally due to the high lipophilicity of the compound. In such cases a computed value was used. The shake-vial experimental measurements performed in-house were all conducted at least in duplicate, in amber glass vials and, in some cases, with varying ratios of octanol and MOPS buffer, mutually pre-saturated prior to the experiment. Overnight shaking was used. HPLC analysis at different wavelengths, after centrifugation and separation of the phases, was used for the quantitative analysis, using both phases.

Statistical Analysis

All regression analyses were performed via the JMP software (v. 3.2.1, SAS Institute, SAS Campus Drive, Cary, N.C. 27513). Ten compounds were selected across the set of 36 compounds, covering the entire range of lipophilicity, to monitor the day-to-day performance of the method. Statistical calculations showed that the use of the 10 compounds would assure that the estimated slope, in the final regression equation, would be within ±0.09 of true one. The JMP software was also used for the Quality Monitoring. Data accumulated for the standard set of compounds, and regularly plotted on the control charts, constitute a powerful method for the detection of trends and variations in performance. Variations in $log k_w$ values, for the selected compounds, should not exceed ±3 $k_s$, where $k_s$ is the standard deviation estimate based on data collected under well controlled experiments. A control chart for nifuroxime is shown in FIG. 5.

TABLE 1

Retention time and logP$_{oct}$ data for the 36 solutes used.

| Compound | CAS # | log k'$_2$[a] | ElogP$_{oct}$[b] | logP$_{oct}$[c] | Residual | Refs.[d] |
|---|---|---|---|---|---|---|
| 3,5-Dichlorophenol | 591-35-5 | 3.40 | 3.91 | 3.68 | −0.23 | 9 |
| 3-Bromoquinoline | 5332-24-1 | 2.54 | 2.95 | 3.03 | 0.08 | 9 |
| 3-Clorophenol | 108-43-0 | 2.49 | 2.90 | 2.50 | −0.40 | 18 |
| Acetaminophen | 103-90-2 | −0.02 | 0.11 | 0.51 | 0.40 | 19 |
| Acetophenone | 98-86-2 | 1.31 | 1.59 | 1.58 | −0.01 | 18 |
| Allopurinol | 315-30-0 | −0.89 | −0.85 | −0.55 | 0.30 | 20 |
| Bromazepam | 1812-30-2 | 1.13 | 1.39 | 1.65 | 0.26 | 21 |
| Carbamazepine | 298-46-4 | 1.70 | 2.02 | 2.19 | 0.17 | 22 |
| Chloramphenicol | 56-75-7 | 1.18 | 1.44 | 1.14 | −0.30 | 23 |
| Clotrimazole | 23593-75-1 | 4.13 | 4.72 | 5.20 | 0.48 | Footnote e |
| Dexamethasone | 50-02-2 | 2.03 | 2.39 | 1.83 | −0.56 | 24 |
| Diazepam | 439-14-5 | 2.63 | 3.05 | 2.79 | −0.26 | 25 |
| Estradiol | 50-28-2 | 3.34 | 3.84 | 4.01 | 0.17 | 23 |
| Fluconazole | 86386-73-4 | 0.37 | 0.54 | 0.5 | −0.04 | 17 |
| Griseofulvin | 126-07-8 | 2.21 | 2.59 | 2.18 | −0.41 | 23 |
| Hydrocortisone | 50-23-7 | 1.43 | 1.72 | 1.55 | −0.17 | 24 |
| Hydrocortisone-21-acetate | 50-03-3 | 1.93 | 2.27 | 2.19 | −0.08 | 24 |
| Lorazepam | 846-49-1 | 2.36 | 2.75 | 2.51 | −0.24 | 26 |
| Lormetazepam | 848-75-9 | 2.40 | 2.80 | 2.72 | −0.08 | 27 |
| Naphthalene | 91-20-3 | 3.06 | 3.53 | 3.37 | −0.16 | 23 |
| Nifedipine | 21829-25-4 | 2.46 | 2.86 | 3.17 | 0.31 | This work |
| Nifuroxime | 6236-05-1 | 1.11 | 1.36 | 1.28 | −0.08 | This work |
| Prednisolone | 50-24-8 | 1.54 | 1.84 | 1.60 | −0.24 | This work |
| Prednisone | 53-03-2 | 1.21 | 1.48 | 1.46 | −0.02 | 23 |
| Quinoline | 91-22-5 | 1.56 | 1.86 | 2.03 | 0.17 | 28 |
| Testosterone | 58-22-0 | 2.74 | 3.17 | 3.29 | 0.12 | 24 |
| Tolnaftate | 2398-96-1 | 4.55 | 5.18 | 5.40 | 0.22 | Footnote e |
| Antipyrine | 60-80-0 | 0.09 | 0.23 | 0.38 | 0.15 | 29 |
| Bifonazole | 60628-96-8 | 4.37 | 4.98 | 4.77 | −0.21 | 23 |
| Caffeine | 58-08-2 | −0.31 | −0.21 | −0.07 | 0.14 | 23 |
| Diethylstilbestrol | 56-53-1 | 4.16 | 4.75 | 5.07 | 0.32 | 23 |
| Methylthiolnosine | 342-69-8 | 0.19 | 0.34 | 0.09 | −0.25 | This work |
| Metronidazole | 443-48-1 | −0.32 | −0.22 | −0.02 | 0.20 | 30 |
| Nitrofurazone | 59-87-0 | 0.10 | 0.24 | 0.23 | −0.01 | 31 |
| Pentoxifylline | 6493-05-6 | 0.16 | 0.31 | 0.29 | −0.02 | 32 |
| Thiamphenicol | 15318-45-3 | −0.24 | −0.13 | −0.27 | −0.14 | 33 | a. Average of at least three determinations on different LC-ABZ columns. b. Data from Equation 3.
c. Shake-flask data. d. References for shake flask data. e. Computed values using ClogP 3.55 v.210.

TABLE 2

Solvation parameters for 34 solutes.

| Compound | R$_2$ | π$_2^H$ | Σα$_2^H$ | Σβ$_2^O$ | Vx |
|---|---|---|---|---|---|
| 3,5-Dichlorophenol | 1.02 | 1.00 | 0.91 | 0.00 | 1.0199 |
| 3-Bromoquinoline | 1.64 | 1.23 | 0.00 | 0.42 | 1.2193 |
| 3-Chlorophenol | 0.91 | 1.06 | 0.69 | 0.15 | 0.8975 |
| Acetominophen | 1.06 | 1.63 | 1.04 | 0.86 | 1.1724 |
| Acetophenone | 0.82 | 1.01 | 0.00 | 0.48 | 1.0139 |
| Allopurinol | 1.41 | 1.55 | 0.70 | 0.92 | 0.8818 |
| Bromazepam | 2.31 | 1.38 | 0.33 | 1.62 | 1.9445 |
| Carbamazepine | 2.15 | 2.07 | 0.52 | 1.13 | 1.8106 |
| Chloramphenicol | 1.85 | 0.72 | 0.34 | 2.09 | 2.0728 |
| Clotrimazole | 2.55 | 2.60 | 0.00 | 1.08 | 2.6230 |
| Dexamethasone | 2.04 | 3.51 | 0.71 | 1.92 | 2.9132 |
| Diazepam | 2.08 | 1.57 | 0.00 | 1.25 | 2.0739 |
| Estradiol | 1.80 | 1.77 | 0.86 | 1.10 | 2.1988 |
| Fluconazole | 2.34 | 2.80 | 0.47 | 1.65 | 2.0064 |
| Griseofulvin | 1.75 | 2.69 | 0.00 | 1.50 | 2.3947 |
| Hydrocortisone | 2.03 | 3.49 | 0.71 | 1.90 | 2.7976 |
| Hydrocortisone-21-acetate | 1.89 | 2.88 | 0.46 | 2.16 | 3.0951 |
| Lorazepam | 2.51 | 1.28 | 0.45 | 1.63 | 2.1141 |
| Lormetazepam | 2.44 | 1.65 | 0.12 | 1.61 | 2.2550 |
| Naphthalene | 1.34 | 0.92 | 0.00 | 0.20 | 1.0854 |
| Nifedipine | 1.50 | 2.45 | 0.23 | 1.45 | 2.4945 |
| Prednisolone | 2.21 | 3.10 | 0.71 | 1.92 | 2.7546 |
| Prednisone | 2.14 | 3.58 | 0.36 | 1.89 | 2.7116 |
| Quinoline | 1.27 | 0.97 | 0.00 | 0.54 | 1.0443 |
| Testosterone | 1.54 | 2.59 | 0.32 | 1.19 | 2.3827 |
| Tolnaftate | 2.97 | 2.20 | 0.00 | 0.93 | 2.3949 |
| Antipyrine | 1.32 | 1.50 | 0.00 | 1.48 | 1.5502 |
| Bifonazole | 2.41 | 2.25 | 0.00 | 1.12 | 2.5006 |
| Caffeine | 1.50 | 1.60 | 0.00 | 1.33 | 1.3632 |
| Diethylstilbestrol | 1.60 | 1.75 | 1.26 | 0.77 | 2.2440 |
| Metronidazole | 1.05 | 1.60 | 0.18 | 1.03 | 1.1919 |
| Nitrofurazone | 1.65 | 1.79 | 0.40 | 1.08 | 1.2644 |
| Pentoxifylline | 1.64 | 2.28 | 0.00 | 1.84 | 2.0834 |
| Thiamphenicol | 2.26 | 3.30 | 0.90 | 2.03 | 2.3204 |

FIGURE LEGENDS

FIG. 1. Correlation between logP$_{oct}$ and log k'$_w$ for 27 solutes in the absence of octanol.

FIG. 2. Correlation between logP$_{oct}$ and log k'$_w$ for 27 solutes in the presence of octanol.

FIG. 3. Correlation between logP$_{oct}$ and log k'$_w$ for 36 solutes.

FIG. 4. Plot of residuals vs. logP$_{oct}$

FIG. 5. Control plot for nifuroxime.

What is claimed is:

1. A method of determining ElogP$_{oct}$ for chemical compounds which comprises:

a) Introducing said chemical compounds seriatim to the column of a reverse phase high performance liquid chromatograph; said column being an embedded amide functional group column; or a C-18 bonded column with low silanol activity; and b) Eluting said compounds with a mobile phase containing MOPS buffer and a methanol/octanol mixture in which the proportions of said methanol/octanol mixture to said buffer are from 70 to 15% v/v; and with flow rates between 0.5 and 2 ml/mm and with the proviso that said mobile phase does not contain an aliphatic amine; and c) Measuring the retention time required to elute each sample from said column; and d) Calculating $ElogP_{oct}$ from the retention time of each sample using equation 3:

$$logP_{oct}=1.1021(\pm 0.0291)logk'_{w}+0.1344(\pm 0.0653) \quad \text{(Eq. 3)}.$$

2. The method of claim 1 wherein each of steps a) through d) is preformed by robotic means under the control of a programmed computer.

3. The method of claim 1 wherein said column is a C-18 bonded column with low silanol activity.

4. A method of determining $ElogP_{oct}$ for chemical compounds which comprises:

a) Introducing said chemical compounds seriatim to the column of a reverse phase high performance liquid chromatograph; said column being an embedded amide functional group column; or a C-18 bonded column with low silanol activity; and b) Eluting said compounds with a mobile phase containing MOPS buffer and a methanol/octanol mixture in which the proportions of said methanol/octanol mixture to said buffer are from 70 to 15% v/v; and with flow rates between 0.5 and 2 ml/min and with the proviso that said mobile phase does not contain an aliphatic amine; and c) Measuring the retention time required to elute each sample from said column; and d) Calculation $ElogP_{oct}$ from the retention time of each sample using equation 3:

$$logP_{oct}=1.1021(\pm 0.0291)logk'_{w}+0.1344(\pm 0.00653) \quad \text{(Eq.3)},$$

wherein said compounds for which ElogP.sub.oct is to be determined are divided into groups according to calculated lipophilicity based on chemical structure and; ElogP.sub.oct is determined for all samples in a first group and; said column is equilibrated to the conditions for a second group.

5. The method of claim 4 wherein said compounds are divided into three groups wherein the first group has a calculated $logP_{oct}$ range of 0.5 to 1; the second group has a calculated $logP_{oct}$ range of 1 to 3 and the third group has a calculated $logP_{oct}$ of greater than 3.

6. The method of claim 5 wherein the flow rate and % of methanol are adjusted to the conditions shown below for each $logP_{oct}$ range:

| $logP_{oct}$ Range | Flow rate (mL/min) | % MeOH |
| --- | --- | --- |
| −0.5 to 1 | 0.5 | 15, 20, or 25 |
| 1–3 | 1 | 40, 45, or 50 |
| >3 | 2 | 60, 65, or 70 |

7. The method of claim 6 wherein said $logP_{oct}$ values are calculated by a programmed computer and samples within a defined $logP_{oct}$ range are introduced seriatim into said column by robotic means under control of a programmed computer and calculating and recording each $ElogP_{oct}$ from the retention time of each sample by equation 3.

8. A method of determining $ElogP_{oct}$ for chemical compounds which comprises:

a) Introducing said chemical compounds seriatim to the column of a reverse phase high performance liquid chromatograph; said column being an embedded amide functional group column; or a C-18 bonded column with low silanol activity; and b) Eluting said compounds with a mobile phase containing MOPS buffer and a methanol/octanol mixture in which the proportions of said methanol/octanol mixture to said buffer are from 70 to 15% v/v; and with flow rates between 0.5 and 2 ml/mm and with the proviso that said mobile phase does not contain an aliphatic amine; and c) Measuring the retention time required to elute each sample from said column; and d) Calculating $ElogP_{oct}$ from the retention time of each sample using equation 3:

$$logP_{oct}=1.1021(\pm 0.0291)logk'_{w}+0.1344(\pm 0.0653) \quad \text{(Eq. 3)},$$

wherein said column is an embedded amide functional group column.

* * * * *